(12) United States Patent
Diatchenko et al.

(10) Patent No.: US 8,716,349 B2
(45) Date of Patent: May 6, 2014

(54) COMPOSITIONS AND METHODS FOR THE TREATMENT OF SOMATOSENSORY DISORDERS

(75) Inventors: Luda Diatchenko, Chapel Hill, NC (US); William Maixner, Chapel Hill, NC (US)

(73) Assignee: Algynomics Inc., Chapel Hill, NC (US)

( * ) Notice: Subject to any disclaimer, the term of this patent is extended or adjusted under 35 U.S.C. 154(b) by 179 days.

(21) Appl. No.: 13/076,386

(22) Filed: Mar. 30, 2011

(65) Prior Publication Data
US 2011/0245208 A1 Oct. 6, 2011

Related U.S. Application Data

(60) Provisional application No. 61/318,792, filed on Mar. 30, 2010.

(51) Int. Cl.
*A61K 31/135* (2006.01)
*A61K 31/44* (2006.01)

(52) U.S. Cl.
USPC .......................... 514/653; 514/282; 514/652

(58) Field of Classification Search
None
See application file for complete search history.

(56) References Cited

U.S. PATENT DOCUMENTS

| | | | |
|---|---|---|---|
| 4,668,232 A * | 5/1987 | Cordes et al. ................. | 424/448 |
| 5,908,847 A * | 6/1999 | Eek ................. | 514/282 |
| 6,488,960 B1 | 12/2002 | Bardsley | |
| 6,716,449 B2 * | 4/2004 | Oshlack et al. ............... | 424/449 |
| 8,093,286 B2 | 1/2012 | Liggett et al. | |
| 2003/0050257 A1 | 3/2003 | Gao et al. | |
| 2003/0135202 A1 | 7/2003 | Harper et al. | |
| 2007/0276024 A1 | 11/2007 | Bond | |
| 2008/0096971 A1 | 4/2008 | Baxter et al. | |
| 2009/0156581 A1 | 6/2009 | Dillon et al. | |

FOREIGN PATENT DOCUMENTS

| | | |
|---|---|---|
| EP | 0105996 A1 | 4/1984 |
| GB | 1394542 A | 5/1975 |
| WO | 03097073 A1 | 11/2003 |
| WO | 2007001324 A2 | 1/2007 |
| WO | 2007070252 A2 | 6/2007 |

OTHER PUBLICATIONS

Beck, A., et al., "Plasma Insulin Levels and Beta-Adrenoceptor Antagonists. Relevace of the Steric Configuration of Beta-Adrenoceptor Antagonists to Their Effect on Glucose Tolerance", "Naunyn-Schmiedeberg's Arch Pharmacol", 1983 pp. 46-9, vol. 324.
Baramki, D., et al., "Modulation of T-Cell Function by (R)- and (S)-Isomers of Albuterol: Anti-Inflammatory Influences of (R)-Isomers are . . . ", "J Allergy Clin Immunol", Mar. 2002, pp. 449-454, vol. 109 No. 3 .
Brochet, D., et al., "Antinociceptive activity of beta-adrenoceptor agonists in the hot plate test in mice.", "Psychopharmacology (Berl)", Apr. 1986, pp. 527-528, vol. 88, No. 4 (Abstract).
Emilien, G., et al., "Current Therapeutics Uses and Potential of [Beta]-Adrencoceptor Agonists and Antagonists", "Euro J. Clin Pharmacol", 1998, pp. 389-404, vol. 53, No. 6.
Goleva, E., et al., "Differential Control of TH1 Versus TH2 Cell Responses by the Combination of Low-Dose Steroids With Beta2-Adrenergic . . . ", "J Allergy Clin Immunol", Jul. 2004, pp. 183-191, vol. 114, No. 1 (Abstract).
Huszar, E., et al., "Effects of ketotifen and clenbuterol on beta-adrenergic receptor functions of lymphocytes and on plasma TXB-2 levels . . . ", "Zeitschrift fur Erkrankungen der Atmungsorgane", Jan. 1990, pp. 141-146, vol. 175, No. 3 (Abstract).
Martin, P., et al., "Comparison of Clenbuterol Enantiomers Using Four Psychopharmacological Tests Sensitive to Beta-Agonists", "Eur J Pharmacol", Oct. 1985, pp. 127-129, vol. 117, No. 1 (Abstract).
Traub-Dargatz, J., et al., "Evaluation of Clinical Signs of Disease, Bronchoalveolar and Tracheal Wash Analysis, and Arterial Blood Gas Tensions . . . ", "Am J. Vet Res", Oct. 1992, pp. 1908-1916, vol. 53, No. 10 (Abstract).
Voulgari, P., "Emerging Durgs for Rheumatoid Arthritis", "Expert Opin. Emerging Drugs", Mar. 2008, pp. 175-196, vol. 13, No. 1.
Waldeck, B., et al., "Steric Aspects of Agonism and Antagonism at Beta-Adrenoceptors: Experiments With the Enantiomers of Clenbuterol", "Acta Pharmacol Toxicol (Copenh)", Mar. 1985, pp. 221-227, vol. 56, No. 3 (Abstract).
Baker, J., "The selectivity of β-adrenoceptor antagonists at the human β1,β2 and β3 adrenoceptors", "British Journal of Pharmacology", Jan. 2005, pp. 317-322, vol. 144.
Brahmadevara, N., et al., "α1-Adrenoceptor antagonist properties of CGP 12177A and other β-adrenoceptor ligands: evidence against . . . ", "British Journal of Pharmacology", Jun. 2004, pp. 781-787, vol. 142, No. 4.
Kozlowska, H., et al., "Ligands at β2, β3-, and the Low-Affinity State of β1-Adrenoceptors Block the α1-Adrenoceptor . . . ", "J Cardiovasc Pharmacol", Jul. 2005, pp. 76-82, vol. 46, No. 1.

(Continued)

*Primary Examiner* — Sreeni Padmanabhan
*Assistant Examiner* — Jody Karol
(74) *Attorney, Agent, or Firm* — Hultquist, PLLC; Steven J. Hultquist; Mary B. Grant

(57) ABSTRACT

A method of combating a somatosensory disorder in a subject, comprising administering to the subject an effective amount of a composition comprising bupranolol and/or pharmaceutically acceptable derivative(s) thereof. Compositions useful for such administration are described, including salts, esters, solvates, etc. of tert-butyl[3-(2-chloro-5-methylphenoxy)-2-hydroxypropyl]amine, in which such salt, ester, solvate, etc. compound is in enantiomeric excess or homoenantiomeric in the R isomer thereof, or is formulated with racemic mixtures of the R and S stereoisomers of the salts, esters, solvates, etc. of tert-butyl[3-(2-chloro-5-methylphenoxy)-2-hydroxypropyl]amine. Combination therapy compositions of opioid receptor agonists and such compounds are also described. A method is disclosed of referential genotypic screening of candidate subjects in connection with therapeutic intervention using the compositions of the disclosure to combat the somatosensory disorder.

21 Claims, 6 Drawing Sheets

(56) References Cited

OTHER PUBLICATIONS

Leblais, V., et al., "Comparison of the α-adrenoceptor-mediated effects of β-adrenoceptor ligands in rat pulmonary artery", "Naunyn-Schmiedeberg's Arch Pharmacol.", Jul. 2005, pp. 535-539, vol. 371.

Malinowska, B., et al., "Atypical cardiostimulant β-adrenoceptor in the rat heart: stereoselective antagonism by bupranolol but lack of . . . ", "British Journal of Pharmacology", Aug. 2003, pp. 1548-1554, vol. 139, No. 8.

Ward, R., "Opioid Tolerance to Sedation and Analgesia", "Pediatric Research", Jun. 2000, pp. 705-706, vol. 47, No. 6.

Zelaszczyk, D., et al., "Four Close Bupranolol Analogues Are Antagonists at the Low-Affinity State of β1-Adrenoceptors", "Journal of Physiology and Pharmacology", Mar. 2009, pp. 51-60, vol. 60, No. 1.

Liang, D., et al., "A Genetic Analysis of Opioid-induced Hyperalgesia in Mice", "Anesthesiology", May 2006, pp. 1054-1062, vol. 104.

Light, K., et al., "Adrenergic Dysregulation and Pain With and Without Acute Beta-Blockade in Women With Fibromyalgia and Temporomandibular Disorder", "The Journal of Pain", May 2009, pp. 542-552, vol. 10, No. 5.

Marsland, A., et al., "Phantom limb pain: A case for beta blockers?", "Pain", 1982, pp. 295-297, vol. 12.

Nackley, A., et al., "Catechol-O-methyltransferase inhibition increases pain sensitivity through activation of both beta2- and beta3-adrenergic receptors", "Pain", 2007, pp. 199-208, vol. 128, No. 3.

Soyka, D., et al., "Beta-Adrenozeptorblocker in Neurologie und Psychiatrie", "Pharmazie in Unserer Zeit", 2004, pp. 476-481, vol. 33, No. 6.

Soyka, D., et al., "Beta-Adrenozeptorblocker in Neurologie und Psychiatrie", "Pharmazie in Unserer Zeit", 2004, pp. 476-481 (Machine Translated English Abstract), vol. 33, No. 6.

Stegeren, A., "Beta-blockers in post-traumatic stress disorder: uses and controversies", "Expert Review of Neurotherapeutics", 2005, pp. 699-702, vol. 5, No. 6.

Szczudlik, A., "Beta-adrenoceptor blocking drugs in the treatment of tension headache", "Pain", Poster Sessions Headache, Fifth World Congress on Pain of the International Association for the Study of Pain, Hamburg, FRG, Aug. 2-7, 1987, p. S79, vol. 30, Supplement 1.

\* cited by examiner a. Early Phase b. Late Phase (A) (B) (C) (D)

COMPOSITIONS AND METHODS FOR THE TREATMENT OF SOMATOSENSORY DISORDERS

CROSS-REFERENCE TO RELATED APPLICATION

The benefit of priority of U.S. Provisional Patent Application 61/318,792 filed Mar. 30, 2010 is hereby claimed under the provisions of 35 USC 119.

TECHNICAL FIELD

The present invention relates to compositions and methods for treatment or prophylaxis of somatosensory disorders.

BACKGROUND

Somatosensory disorders involve several chronic clinical conditions that are characterized by the perception of persistent pain, unpleasantness or discomfort in various tissues and regions of the body. Such disorders may be associated with a state of pain amplification as well as psychological distress characterized by high levels of somatization, depression, anxiety and perceived stress. Somatosensory disorders are frequently associated with other comorbid somatosensory conditions.

It is generally accepted that impairments in CNS regulatory processes, as well as a host of other physiological, psychological and interminable factors, can contribute to the pain amplification and psychological dysfunction associated with somatosensory disorders. Genotypic factors also are present, and exert a strong influence on somatosensory processes. As described in International Patent Application Publication WO 2007/001324, individual variations of COMT, ADRB2, and/or ADRB3 genes can be utilized to determine pain response or pain perception characteristics of a subject and to predict susceptibility of the subject to develop somatosensory disorders and somatization.

Thus, it is possible to identify specific genetic polymorphisms that when present in an individual render that person vulnerable to development of somatosensory disorders when subjected to environmental factors such as physical or emotional stress.

As a concomitant undertaking to the characterization and predictive assessment of somatosensory disorders and the identification of individuals susceptible to them, there is a continuing need for effective pharmacological therapeutic agents for the treatment and prophylaxis of such disorders.

SUMMARY

The present invention relates to compositions and methods for the treatment or prophylaxis of somatosensory disorders.

In one aspect, the invention relates to a method of combating a somatosensory disorder in a subject, comprising administering to the subject an effective amount of a composition comprising bupranolol and/or pharmaceutically acceptable derivative thereof.

In another aspect, the invention relates to a method of such type, wherein the subject is identified by a screening process comprising referential genotypic screening indicative of susceptibility to the somatosensory disorder.

A further aspect of the invention relates to a composition for treatment of a somatosensory disorder, comprising (a) bupranolol or a pharmaceutically effective derivative thereof;

(b) a pharmaceutically acceptable carrier; and (c) a second therapeutic agent for the somatosensory disorder.

Another aspect of the disclosure relates to a composition for contemporaneous administration to combat a somatosensory disorder, comprising R-tert-butyl[3-(2-chloro-5-methylphenoxy)-2-hydroxypropyl]amine, or a derivative thereof, and an opioid receptor agonist.

In a further aspect, the disclosure relates to a method of combating hyperalgesia incident to administration of an opioid receptor agonist to a subject, comprising contemporaneously administering to said subject an effective amount to combat said hyperalgesia, of R-tert-butyl [3-(2-chloro-5-methylphenoxy)-2-hydroxypropyl]amine, or a derivative thereof.

Another aspect of the disclosure relates to a method of suppressing opioid agonist-dependent cAMP production in a cellular assay, comprising administration to a cellular population used in said assay of an effective amount of R-tert-butyl [3-(2-chloro-5-methylphenoxy)-2-hydroxypropyl]amine, or a derivative thereof.

A still further aspect of the disclosure relates to a method of modulating ADRB2 and 6TM MOR interaction to mediate analgesia in a subject, comprising administering to the subject an effective amount therefor of R-tert-butyl[3-(2-chloro-5-methylphenoxy)-2-hydroxypropyl]amine, or a derivative thereof.

Other aspects, features and embodiments of the invention will be more fully apparent from the ensuing disclosure and appended claims.

DESCRIPTION

Figure 1A:
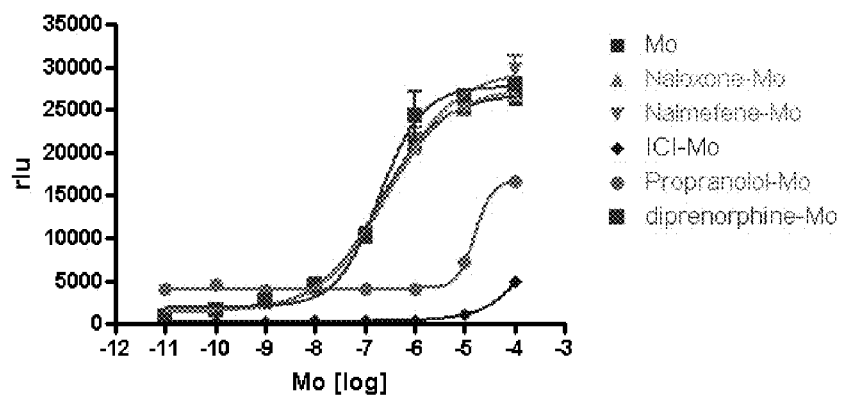
FIG. 1 is a graph of cAMP production as a function of log [morphine], and shows that morphine stimulated cAMP production in cells transfected with ADRB2 in a dose-dependent manner.
FIGS. 1B, 1C, and 1D).

The present invention relates to compositions and methods for the treatment and/or prophylaxis of somatosensory disorders.

As used herein, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the end-points of the broad carbon number range, or as including carbon numbers greater than the lower end-point carbon number and less than the upper end-point carbon number of the range, to constitute various sub-ranges in the various specific embodiments of the invention.

The compounds of the invention may be further specified in specific embodiments by provisos or limitations excluding specific substituents, groups, moieties or structures, in relation to various specifications and exemplifications thereof set forth herein. Thus, the invention contemplates restrictively defined compositions, e.g., a composition wherein $R^i$ is $C_1$-$C_{12}$ alkyl, with the proviso that $R^i \neq C_4$ alkyl when $R^j$ is silyl.

As used herein, "alkyl" refers to straight chain or branched saturated hydrocarbon radicals including $C_1$-$C_{12}$, preferably $C_1$-$C_6$, such as methyl, ethyl, propyl, isopropyl, butyl, s-butyl, t-butyl, pentyl and isopentyl and the like. "Substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like. "Alkenyl" refers to straight chain or branched hydrocarbon radicals including $C_1$-$C_8$, preferably $C_1$-$C_5$ and having at least one carbon-carbon double bond. "Substituted alkenyl" refers to alkenyl radicals further bearing one or more substituent groups as defined above. "Cycloalkyl" refers to saturated or unsaturated, non-aromatic, cyclic ring-containing radicals containing three to eight carbon atoms, preferably three to six carbon atoms, and includes, without limitation, cyclopropyl, cyclobutyl, cyclopentyl, cyclohexyl and the like. "Substituted cycloalkyl" refers to cycloalkyl radicals further bearing one or more substituent groups as defined above. The term "amino" refers to amine groups bearing zero, one, or two alkyl groups, and includes cyclic amines with ring sizes between three and eight carbons. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. "Substituted aryl" refers to aryl radicals further bearing one or more substituent groups as defined above. "Alkylaryl" refers to alkyl-substituted aryl radicals. "Substituted alkylaryl" refers to alkylaryl radicals further bearing one or more substituent groups as defined above. "Arylalkyl" refers to aryl-substituted alkyl radicals. "Substituted arylalkyl" refers to arylalkyl radicals further bearing one or more substituent groups as defined above. "Heterocyclyl" refers to saturated or unsaturated cyclic radicals containing one or more heteroatoms (e.g., O, N, S) as part of the ring structure and having two to seven carbon atoms in the ring. "Substituted heterocyclyl" refers to heterocyclyl radicals further bearing one or more substituent groups as defined above.

In all chemical formulae herein, a range of carbon numbers will be regarded as specifying a sequence of consecutive alternative carbon-containing moieties, including all moieties containing numbers of carbon atoms intermediate the endpoint values of carbon number in the specific range as well as moieties containing numbers of carbon atoms equal to an endpoint value of the specific range, e.g., $C_1$-$C_6$, is inclusive of $C_1$, $C_2$, $C_3$, $C_4$, $C_5$ and $C_6$, and each of such broader ranges may be further subdivided to specify sub-ranges thereof bounded by specific carbon numbers in such broader ranges. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

The invention, as variously described herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the invention.

The aromatic and/or heteroaromatic rings in the compounds described herein can optionally be substituted with from one to three substituents, Z, at any free position. Representative substituents, Z, include $C_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)O R", —SO$_2$R', —SO$_2$NR'R", and —NR'SO$_2$R", where R' and R" are individually hydrogen, C$_{1-6}$ alkyl, cycloalkyl, heterocyclyl, aryl, or arylalkyl (such as benzyl).

In the compounds described herein, aryl rings can be substituted with pyridine or pyrimidine rings, or with 5-membered heteroaryl rings such as thiophene, pyrrole, furan, and imidazole.

The compounds described herein can be prepared from commercially available starting materials, by a variety of synthetic methodologies, related to the particular moieties and the particular substitution desired. The variation in synthetic methodology will be readily apparent to those of skill in the art of organic synthesis. Further, the specific compounds described herein can be derivatized within the skill of the art, based on the disclosure herein.

Thus, those skilled in the art will readily understand that incorporation of other substituents onto the aryl or heteroaryl rings used as a starting material to prepare the compounds described herein can be readily realized. Also, various substituents can be added after the framework has been prepared. Such substituents can provide useful properties in and of themselves or serve as a functional moiety for further synthetic elaboration.

Substituents typically can be added to any precursors to the compounds before they are converted to final products. One proviso is that such substitution should survive the synthesis conditions, or a suitable protecting group employed that is removed after the synthesis is complete.

For example, aryl rings can be halogenated using various known procedures, which vary depending on the particular halogen. Examples of suitable reagents include bromine/water in concentrated HBr, thionyl chloride, pyr-ICl, fluorine and Amberlyst-A. A number of other analogs, bearing substituents in a diazotized position of an aryl ring, can be synthesized from the corresponding aniline compounds, via the diazonium salt intermediate. The diazonium salt intermediates can be prepared using known chemistry, for example, treatment of aromatic amines such as aniline with sodium nitrite in the presence of a mineral acid.

Diazonium salts can be formed from anilines, which in turn can be prepared from nitrobenzenes (and analogous amine-substituted heteroaryl rings can be prepared from nitro-substituted heteroaryl rings). The nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art. For example, hydroxy-triphenyl methane analogues can be prepared by reacting the diazonium salt intermediate with water, protecting the resulting hydroxyl group, forming the cyclopentadienyl anion, and reacting it with a suitable aldehyde or ketone. Likewise, alkoxy triphenyl methane analogues can be made by reacting the diazonium salt with alcohols. The diazonium salt can also be used to synthesize cyano or halo compounds, as will be known to those skilled in the art. Mercapto substitutions can be obtained using techniques described in Hoffman et al., J. Med. Chem. 36: 953 (1993). The mercaptan so generated can, in turn, be converted to an alkylthio substituent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, Org. React. (N.Y.) 42: 335 (1992) and Hughes, Org. Prep. Proced. Int. 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Similarly, benzene rings (and pyridine, pyrimidine, pyrazine, and other heteroaryl rings) can be substituted using known chemistry, including the reactions discussed above. For example, the nitro group on nitrobenzene can be reacted with sodium nitrite to form the diazonium salt, and the diazonium salt manipulated as discussed above to form the various substituents on a benzene ring.

Illustrative Aspects

The present disclosure relates to therapeutic agents that are β2-adrenergic receptor antagonists, and when administered affect pain processing systems determining pain sensitivity and pain response in a subject. β-adrenergic receptor stimulation evokes expression/release of pro-inflammatory cytokines and growth factors.

The therapeutic agents of the present disclosure are usefully administered as pain-preventative and/or pain-ameliorative agents for a variety of pain conditions, including, in specific embodiments and applications, acute pain from trauma, acute operative and post-operative pain, referred pain, spontaneous pain, hyperalgesia, and allodynia. Therapeutic agents of the present disclosure include compounds that exhibit sensitivity and selectivity for ADRB1, ADRB2, ADRB3 and ADRA1 receptors.

Therapeutic agents of the present disclosure may be utilized in specific applications and for specific indications as single administered therapeutic agents, and in other applications and indications may be employed to potentiate effects of other pain-preventative and/or pain-ameliorative agents of widely varying types, including opioids, glutamate receptor antagonists, α-1A adrenergic receptor antagonists, norepinephrine-specific reuptake inhibitors, serotonin-specific reuptake inhibitors, non selective serotonin and norepinephrine reuptake inhibitors, tricyclic antidepressants, calcium channel blockers, hyperalgesia blockers, non-steroidal anti-inflammatory drugs, allodynia therapeutics, muscle relaxants, etc.

The therapeutic agents of the present disclosure can be utilized to combat opioid-induced hyperalgesia that limits the use of opioids, as well as to diminish pain that would otherwise be addressed by administering opioid drugs, thereby enabling dosages of administered opioids to be significantly reduced. Such agents may also have application in reducing the pharmacological tolerance to opioid drugs thereby enabling lower therapeutic dosages of an administered opioid. These agents may also reduce the adverse cardiovascular, respiratory, and gastrointestinal side effects of opioids, thereby enabling higher doses of an administered opioid to be tolerated. Such agents may also have application in combating opioid drug addiction and abuse. In other applications, the therapeutic agents of the present disclosure have utility as screening agents in cellular assays for identification of compounds and compositions that modulate cAMP production The invention in one aspect contemplates a method of combating a somatosensory disorder in a subject, including administering to the subject an effective amount of a composition comprising bupranolol and/or pharmaceutically acceptable derivative thereof.

Such method may be carried out to combat a somatosensory disorder, or more than one such disorder, selected from among chronic pain conditions, idiopathic pain conditions, fibromyalgia syndrome, myofascial pain disorders, tension headache, migraine headache, phantom limb sensations, irritable bowel syndrome, chronic lower back pain, back pain, chronic fatigue syndrome, multiple chemical sensitivities, temporomandibular joint disorder, post-traumatic stress disorder, chronic idiopathic pelvic pain, Gulf War Syndrome, vulvar vestibulitis, osteoarthritis, rheumatoid arthritis, neuropathic pain, and angina pectoris.

The method may utilize a composition comprising a pharmaceutically acceptable derivative of bupranolol, selected from among pharmaceutically acceptable bupranolol salts, bupranolol esters, bupranolol solvates, and prodrugs of bupranolol, e.g., a pharmaceutically acceptable bupranolol salt or a pharmaceutically acceptable bupranolol ester.

The administering of the bupranolol and/or pharmaceutically effective derivative thereof may include, in specific implementations, oral administration, parenteral administration, non-parenteral administration, transdermal administration, or injection administration.

In carrying out the method of the invention, the subject to whom the bupranolol and/or pharmaceutically effective derivative thereof is administered may be identified in the first instance by a screening process comprising referential genotypic screening indicative of susceptibility to the somatosensory disorder, as hereinafter more fully described.

Such referential genotypic screening indicative of susceptibility to the somatosensory disorder may be carried out by determining a genotype of a candidate subject with respect to a gene selected from the group consisting of ADRB2, ADRB3, COMT, and combinations thereof, and comparing the genotype of the candidate subject with at least one reference genotype associated with the susceptibility to develop the somatosensory disorder, wherein the reference genotype is selected from the corresponding group consisting of an ADRB2 genotype, an ADRB3 genotype, a COMT genotype, and combinations thereof.

The somatosensory disorder for which the referential genotypic screening is performed may include a somatosensory disorder selected from among chronic pain conditions, neuropathic pain conditions, idiopathic pain conditions, fibromyalgia syndrome, myofascial pain disorders, tension headache, migraine headache, phantom limb sensations, irritable bowel syndrome, chronic lower back pain, back pain, chronic fatigue syndrome, multiple chemical sensitivities, temporomandibular joint disorder, post-traumatic stress disorder, chronic idiopathic pelvic pain, Gulf War Syndrome, vulvar vestibulitis, osteoarthritis, rheumatoid arthritis, and angina pectoris.

The invention in a further aspect relates to a composition for treatment of a somatosensory disorder, in which the composition includes (a) bupranolol or a pharmaceutically effective derivative thereof, (b) a pharmaceutically acceptable carrier, and (c) a second therapeutic agent for the somatosensory disorder. The second therapeutic agent may be selected from among analgesic agents, anti-inflammatory agents, adrenergic receptor beta-2 (ADBR2) antagonists, adrenergic receptor beta-3 (ADBR3) antagonists, and catechol-O-methyl-transferase (COMT) modulators.

Somatosensory Disorders and Therapeutic Compositions

The somatosensory disorders for which the compositions of the present invention are usefully employed are clinical conditions characterized by the perception of persistent pain, discomfort or unpleasantness in various regions of the body. These conditions are generally, but not always, associated with enhanced sensitivity to pain. On occasion, these conditions are observed without currently known measures of tissue pathology. Exemplary somatosensory disorders include, without limitation, chronic pain conditions, neuropathic pain conditions, idiopathic pain conditions, fibromyalgia syndrome, myofascial pain disorders, tension headache, migraine headache, phantom limb sensations, irritable bowel syndrome, chronic back pain, chronic fatigue syndrome, chemical sensitivities, temporomandibular joint disorder, post-traumatic stress disorder, chronic idiopathic pelvic pain, Gulf War Syndrome, vulvar vestibulitis, osteoarthritis, rheumatoid arthritis, and angina pectoris. A general characteristic of a specific somatosensory disorder is that it can be associated with at least one additional or multiple comorbid somatosensory disorders.

Compositions of the invention include bupranolol and/or a pharmaceutically acceptable derivative thereof as an active therapeutic agent, and a pharmaceutically acceptable carrier and/or excipient(s). Bupranolol, tert-butyl[3-(2-chloro-5-methylphenoxy)-2-hydroxypropyl]amine, as utilized in the practice of the present disclosure, is a nonselective adrenergic beta-2 antagonist and competitive α-1 adrenoceptor antagonist, having the formula:

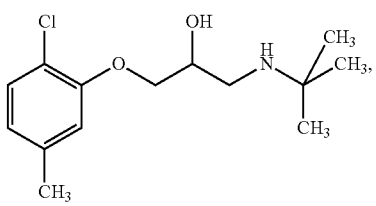 [SMILES: Cc1ccc(Cl)c(OCC(O)CNC(C)(C)C)c1]

wherein the bupranolol contains the R stereoisomer, either in a racemic mixture, in mixtures in which there is an enantiomeric excess of the R stereoisomer, or in an enantiopure composition of the R stereoisomer.

Pharmaceutically acceptable derivatives of bupranolol include any pharmaceutically acceptable bupranolol salts, bupranolol esters, bupranolol solvates, and prodrugs (e.g., esters or carbamates) of bupranolol, which upon administration to a recipient are capable of providing, directly or indirectly, bupranolol or an active metabolite or residue thereof. Such derivatives are recognizable to those skilled in the art, without undue experimentation, and are for example readily prepared in accordance with the techniques and methods described in Burger's Medicinal Chemistry and Drug Discovery, 5th Edition, Vol 1: Principles and Practice, as well as other sources in the medicinal synthetic chemistry art.

In one aspect of the invention, pharmaceutically acceptable derivatives are salts, sulfates, esters and carbamates. In another aspect of the invention, pharmaceutically acceptable derivatives are salts, solvates and esters. In a further aspect, pharmaceutically acceptable derivatives are salts and solvates. In a still further aspect, pharmaceutically acceptable derivatives are salts and esters. In a still further aspect, pharmaceutically acceptable derivatives are salts. In one embodiment, the pharmaceutically acceptable derivatives include bupranolol hydrochloride salts, e.g., R,S-(±)-bupranolol hydrochloride, or R-(+)-bupranolol hydrochloride.

Esters of bupranolol include those that break down readily in the body to yield the parent acid or the salt thereof. An ester may be formed at the hydroxyl (OH) group of bupranolol utilizing methods known in the art involving reaction with the corresponding acid. Esters may be $C_1$-$C_6$ alkyl esters, including methyl esters, ethyl esters, propyl esters, butyl esters, pentyl esters, and hexyl esters. Esters of bupranolol and its derivatives can be utilized in the broad practice of the present disclosure to formulate extended release compositions in which the half-life of such compounds is significantly extended, with concomitant reduction of first pass clearance levels, in administration of corresponding compositions.

Pharmaceutically acceptable salts include salts that retain the biological activity of bupranolol and are not toxicologically contraindicated. Pharmaceutically acceptable salts include both acid addition salts and base addition salts. Suitable salts are described in Berge et al, J. Pharm. Sci., 1977, 66, 1-19. Pharmaceutically acceptable salts include inorganic acid addition salts such as sulfate, phosphate, and nitrate; organic acid addition salts such as acetate, dichloroacetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine.

Bupranolol compounds of the invention, i.e., bupranolol and pharmaceutically acceptable derivatives thereof, may exist in a solid-state in either amorphous or crystalline form, or as a mixture thereof. Solvates of such compounds may be formed in which solvent molecules are incorporated into the crystalline lattice during crystallization. Solvents may include water, ethanol, isopropanol, dimethyl sulfoxide (DMSO), acetic acid, ethanolamine, ethyl acetate, or other suitable solvents or solvent mixtures.

Bupranolol derivative compounds may also be formed in a combination of substituents which creates a chiral center or another form of an isomeric center. In such embodiment, the compound may exist as a racemic mixture, a pure enantiomer, and any enantiomerically enriched mixture. The compounds can occur in varying degrees of enantiomeric excess, and racemic mixtures can be purified using known chiral separation techniques.

Other bupranolol analogs for use in specific applications of the present disclosure include compounds of the formula:

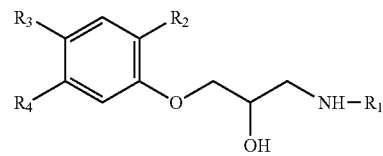

wherein $R_1$ is t-butyl or

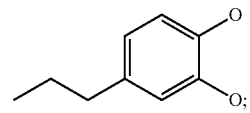

$R_2$ is H, chloro, or methyl;

$R_3$ is H, chloro or methoxy; and $R_4$ is H or methyl, wherein such derivative compound is a $\beta_2$-adrenoceptor antagonist having analgesia-mediating properties.

Specific additional derivatives of bupranolol include the compounds set out below and identified as compounds DZ-51, GD-6, DZ-52 and DZ-13.

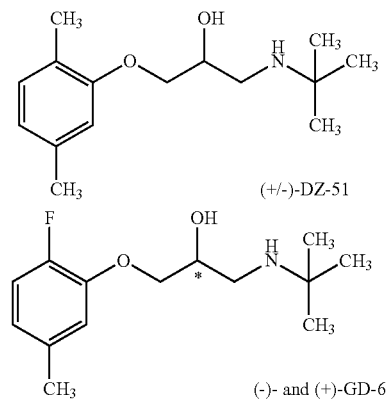

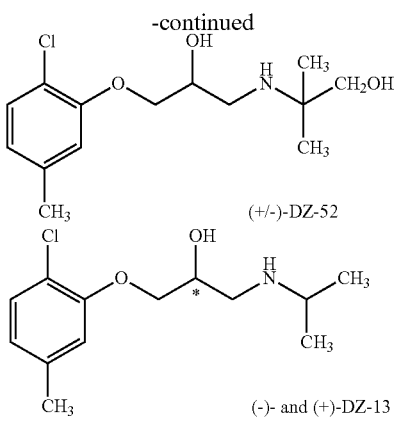

(+/-)-DZ-52

(-)- and (+)-DZ-13

The invention contemplates pharmaceutical compositions including an amount of bupranolol and/or pharmaceutically acceptable derivative thereof that is effective for combating a somatosensory disorder, optionally with at least one additional somatosensory disorder-combating therapeutic agent, and a pharmaceutically acceptable carrier and/or excipient(s). Useful excipients may include, without limitation, diluents, buffers, flavoring agents, disintegrants, surface active agents, thickeners, lubricants, preservatives (including antioxidants), and the like.

Optional additional somatosensory disorder-combating therapeutic agents that can be included in the pharmaceutical composition include, without limitation, analgesic and/or anti-inflammatory agents, adrenergic receptor beta-2 (ADBR2) antagonists, adrenergic receptor beta-3 (ADBR3) antagonists, catechol-O-methyltransferase (COMT) modulators, and/or any other therapeutic agents effective in preventing, ameliorating or therapeutically resolving the somatosensory disorder and/or its symptoms.

The second therapeutic agent can include any of the following illustrative agents, or combinations of two or more thereof:

analgesic agents selected from among acetaminophen, codeine, etorphine, hydromorphone, methadone, morphine, fentanyl, levorphanol, meperidine, oxycodone, propoxyphene, hydrocodone, tramadol, nalbuphine, butorphanol, pentazocine, buprenorphine, naloxone, naltrexone, and nalmefene;

anti-inflammatory agents selected from among aspirin, salicylic acid, celecoxib, diclofenac, diflunisal, ibuprofen, fenoprofen, ketoprofen, oxaprozin, indomethacin, meloxicam, piroxicam, mefenamic acid, nabumetone, naproxen, sulindac, etodolac, ketorolac, and tolmetin;

adjunctive analgesics selected from among baclofen, carbamazepine, carisoprodol, cyclobenzaprine, lamotrigine, orphenadrine, phenyloin, valproate, levetriracetam, methocarbamol, metaxalone, diazepam, clonazepam, lorazepam, alprazolam, tizanidine, gabapentin, pregabalin, topiramate, amitriptyline, desipramine, duloxetine, milnacipran, nortriptyline, paroxetine, citalpram, buprorion, venlafaxine, zonisamide, clonidine, dextromethorphan, ketamine, anantadine, memantine, dronabinol, tetrahydrocannabinol, and cannabidiol;

adrenergic receptor beta-2 (ADBR2) antagonists selected from among adrenergic receptor beta-2 antagonists that may be usefully employed in such pharmaceutical compositions in various embodiments of the invention include, without limitation, butoxamine [DL-erythro-α-(2,5-dimethoxyphenyl)-13-t-butyl aminopropanol hydrochloride], ICI 118,551 [(-)-1-(2,3-[dihydro-7-methyl-1H-inden-4-yl]oxy)-3-([1-methylethyl]-amino)-2-butanol], H35/25 [1-(4'-methylphenyl)-b2,2-1-isopropylaminopropanol], estrogen propranolol, sotalol, timolol, carteolol, carvedilol, nadolol, penbutolol, labetalol, and pindolol;

adrenergic receptor beta-3 (ADBR3) antagonists selected from among L 748337 [(S)-Λ/-[4-[2-[[3-[3-(acetamidomethyl)phenoxy]-2-hydroxypropyl]amino]ethyl]phenyl]benzenesulfonamide], CL 316234 [disodium (R,R)-5-(2-[{2-(3-chlorophenyl)~2-hydroxyethyl}-amino]propyl)-1,3-benzodioxole-2,2,dicarboxylate], SR 59230A [(1-(2-ethylphenoxy)-3-[[(1S)-1,2,3,4-tetrahydro-1-naphthalenyl]amino]-(2S)-2-propanol)]; and catechol-O-methyltransferase (COMT) modulators selected from among S-adenosylmethionine (SAMe), estrogen compounds, progesterone and clonidine.

The compositions and usages herein of bupranolol can be effectuated with salts, esters, solvates, etc. of tert-butyl[3-(2-chloro-5-methylphenoxy)-2-hydroxypropyl]amine, preferably wherein such compound is in enantiomeric excess or homoenantiomeric in the R isomer thereof. The compositions and methods can also be practiced with racemic mixtures of the R and S stereoisomers of the salts, esters, solvates, etc. of tert-butyl[3-(2-chloro-5-methylphenoxy)-2-hydroxypropyl] amine.

The disclosure in another aspect relates to the use of bupranolol as a therapeutic agent for combating the occurrence of hyperalgesia incident to the use of opioid analgesics, e.g., morphine. We have established that the $\beta_2$-adrenergic receptor (ADRB2) facilitates cell surface expression of 6-transmembrane (6TM) mu-opioid receptor (MOR) of either isoform, and that ADRB2 physically interacts with 6TM MOR, whereby cellular activities of ADRB2 and 6TM MOR are interdependent in character. It is known that MOR agonists such as morphine can mediate opioid-induced hyperalgesia facilitated by related cellular excitatory effects involving increases in production of cyclic adenosine monophosphate (cAMP). 6TM MOR effects have been demonstrated to be at least one of the cellular mechanisms facilitating opioid-dependent cellular excitatory action. We have demonstrated that bupranolol as a selective ADRB2 antagonist is an effective blocker of morphine- and other opioid agonist-dependent cellular excitatory effects.

Accordingly, the disclosure contemplates the use of bupranolol or bupranolol derivative as a therapeutic agent that can be contemporaneously administered with an opioid receptor agonist, wherein the bupranolol or bupranolol derivative acts to suppress opioid-dependent cAMP production and to promote analgesia. As used in such context, the term "contemporaneously administered" means that the bupranolol or bupranolol derivative is administered to a subject simultaneously with the mu-opioid agonist, e.g., as a co-dosed therapeutic agent, or within a period of 8 hours before or after administration of the mu-opioid agonist to the subject.

Such usage of bupranolol or bupranolol derivative as a result of its independent analgesic character can result in significant reduction in the dosage amounts of opioid receptor agonists that are required to be administered to a subject for the prevention or amelioration of pain. As used herein, the term "opioid receptor agonists" is intended to be broadly construed to encompass agents that are agonistic at opioid receptors, including mu, delta and kappa receptors. In various embodiments, such opioid receptor agonists include mu-opioid receptor agonists, e.g., morphine.

The disclosure in another aspect relates to a method of screening for agents that modulate cAMP production in a subject, comprising cellular assays in which bupranolol or a bupranolol derivative is applied to the cells utilized in such assay, to facilitate identification of the nature and extent of modulation of cAMP production by a candidate agent, e.g., as a potential analgesic.

A further aspect of the disclosure relates to a therapeutic composition comprising an opioid receptor agonist in combination with bupranolol or bupranolol derivative, wherein the bupranolol or bupranolol derivative is in a form that is effective to combat excitatory and/or hyperalgesic effects occurring in the absence of bupranolol or bupranolol derivative. In one specific embodiment, the therapeutic composition comprises a mu-opioid agonist in combination with a salt or ester of tert-butyl[3-(2-chloro-5-methylphenoxy)-2-hydroxypropyl]amine, preferably wherein such compound is in enantiomeric excess or homoenantiomeric in the R isomer thereof.

A still further aspect of the disclosure relates to a method of modulating ADRB2 and 6TM MOR interaction to mediate analgesia in a subject, comprising administering to the subject an effective amount therefor of tert-butyl[3-(2-chloro-5-methylphenoxy)-2-hydroxypropyl]amine, preferably wherein such compound is in enantiomeric excess or homoenantiomeric in the R isomer thereof.

Compositions of the therapeutic agents of the present disclosure may be employed as antineoplastic compositions to combat tumoral or oncological conditions, in specific applications. In other applications, the therapeutic agents of the present disclosure are used to block or at least partially prevent or ameliorate tolerance and/or dependency effects of opioids, e.g., mu-opioids, such as morphine. The disclosure correspondingly contemplates combination therapies and combination formulations of bupranolol or bupranolol derivatives for such indications.

Illustrative usage of bupranolol and bupranolol derivatives in the broad practice of the present disclosure may include administration for pain management of conditions including, without limitation, temporomandibular disorder, headache, fibromyalgia, lower back pain, back pain, injury-evoked pain such as whiplash, post-traumatic stress disorder, inflammatory bowel syndrome, interstitial cystitis, chronic pelvic pain, vulvar vestibulitis syndrome, osteoarthritis, rheumatoid arthritis, neuropathic pain, and the like, as well as for surgical and post-surgical pain management, e.g., post-operative pain management with or without opioid administration.

Administration and Formulations

The invention further contemplates various methods of combating a somatosensory disorder, comprising administering to a subject in need thereof of an effective amount of a pharmaceutical composition of the invention, by various administrative modalities and techniques.

Subjects to be treated by the compounds of the present invention include both human and non-human animal (e.g., bird, dog, cat, cow, horse) subjects, and are preferably mammalian subjects, and most preferably human subjects.

Pharmaceutical compositions of the invention can be administered orally, e.g., in a liquid form within a solvent such as an aqueous or non-aqueous liquid, or within a solid carrier. Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The pharmaceutical compositions thus can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. For example, liquid preparations can be prepared with suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

The pharmaceutical compositions of the invention can also be administered via injection, i.e., intravenously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

Pharmaceutical compositions of the invention can also be administered using other means, for example, rectal administration. Formulations useful for rectal administration, such as suppositories, are well known to those of skill in the art. The compositions can also be administered by inhalation (e.g., in the form of an aerosol either nasally or using delivery articles of the type set forth in U.S. Pat. No. 4,922,901 to Brooks et al.; topically (e.g., in lotion form); or transdermally (e.g., using a transdermal patch). Although it is possible to administer the compounds in the form of bulk active chemical compounds, it is preferred to present the compounds in the form of pharmaceutical compositions for efficient and effective administration.

The pharmaceutical compositions of the invention therefore include those suitable for parenteral as well as non-parenteral administration, and specific administration modalities include, but are not limited to, oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Compositions suitable for oral and parenteral administration are preferred, with compositions suitable for oral administration most preferred. Intranasal formulations can be utilized in which a liquid composition containing bupranolol or bupranolol derivative is aerosolized or nebulized, or carrier particles of appropriate size to achieve effective pulmonary treatment.

Polymer-based extended release formulations, as well as extended release dose forms in general, are contemplated for bupranolol and/or bupranolol derivatives in the broad practice of the present disclosure, in specific applications to achieve a predetermined duration of action, and appropriate pharmacokinetic profiles for effective treatment.

Exemplary methods for administering such compositions will be apparent to the skilled persons in the art. The degree of usefulness of these formulations may depend on the particular composition used and the particular subject receiving the treatment. These formulations may contain a liquid carrier that may be oily, aqueous, emulsified or contain certain solvents suitable to the mode of administration.

The compositions of the invention can be administered intermittently or at a gradual, continuous, constant or controlled rate to a subject to be treated. In addition, the time of day and the number of times per day that the pharmaceutical composition is administered can vary.

By way of example, compounds of the present invention may be administered in specific embodiments of the invention at a dosage between about 0.1 and 200 mg/kg body weight, preferably between about 1 and 90 mg/kg body weight, and more preferably between about 10 and 80 mg/kg body weight. The present disclosure also contemplates ultra-low dose administration of therapeutic agents of the disclosure, e.g., down to low milligram and even picogram levels in some instances.

The invention also contemplates combination or alternation therapy in which the pharmaceutical composition including the bupranolol and/or a pharmaceutically effective derivative thereof is administered in combination or alternation with another somatosensory disorder-combating therapy. In general, in combination therapy, effective dosages of two or more therapeutic agents are administered together, whereas during alternation therapy, an effective dosage of each therapeutic agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

By way of illustration, the dosage regimen for oral administration in accordance with one specific embodiment of the disclosure includes administration of 50 milligrams of bupranolol twice daily, which can be varied, e.g., increased to 100 milligrams four times daily, as necessary or desirable for effective treatment.

Genotypic Screening

The invention in a further aspect contemplates a method of combating a somatosensory disorder in a subject by administration of an effective amount of bupranolol or a pharmaceutically acceptable derivative of bupranolol, in which the subject is first selected for such administration by a referential genotypic screening process of a type as described in International Patent Application Publication WO 2007/001324.

In such genotypic screening process, the susceptibility to a somatosensory disorder of a candidate subject is established, by determining a genotype of the candidate subject with respect to a gene selected from the group consisting of ADRB2, ADRB3, COMT, and combinations thereof; and the genotype of the candidate subject is compared with at least one reference genotype associated with the susceptibility to develop the somatosensory disorder, wherein the reference genotype is correspondingly selected from the group consisting of an ADRB2 genotype, an ADRB3 genotype, a COMT genotype, and combinations thereof.

Upon determining from the candidate subject's genotype that the candidate subject is susceptible to the somatosensory disorder for which the determination was made, the candidate subject becomes a subject, and is administered the effective amount of bupranolol or a pharmaceutically acceptable derivative thereof, to combat such somatosensory disorder.

The features and advantages of the compositions and methods of the present disclosure are more fully shown by the ensuing non-limiting examples.

Example 1

Experimental Procedure

Assessment of intracellular cAMP levels was performed using a GloSensor cAMP-sensitive luciferase reporter (Promega). HEK-293 cells co-expressing GloSensor-22F and receptor isoforms were seeded in white, 384-well plates for 24 hours. The following day, the medium was replaced with GloSensor reagent (Promega), and incubated for two hours. Cells were then challenged with morphine or other agonists at various concentrations. Luminescence was read on a Victor (Perkin Elmer) plate counter after 5 minutes. When antagonist treatment was done, cells were pre-treated with the antagonist compounds for 30 minutes prior to agonist treatment. Results are shown in FIGS. 1 to 4.

Figure 1B:
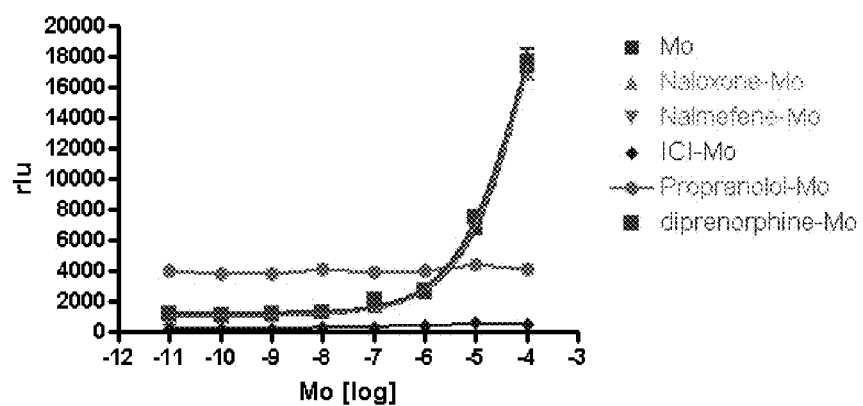

FIG. 1 is a graph of cAMP production as a function of log [morphine], and shows that morphine stimulated cAMP production in cells transfected with ADRB2 in a dose-dependent manner. Both the "−" isomer (FIG. 1A) and "+" isomer (FIG. 1B) of morphine show ADRB2-dependent cAMP stimulation, however, the "−" isomer was about 100 times more potent agonist than the "+" isomer as an agonist of ADRB2. Agonist stimulation was blocked by the non-selective beta-blocker propranolol (100 nM) and the selective ADRB2 antagonist ICI118,551 (300 nM), but not by mu-opiod antagonists naloxone (100 nM), nalmefene (100 nM) or diprenorphine (100 nM). These effects were depended on ADRB2 tranfrection (data not shown). ICI118,551 is 3-(isopropylamino)-1-[(7-methyl-4-indanyl)oxy]butan-2-ol,

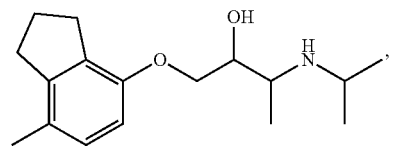 [SMILES: Cc1ccc(OCC(O)C(C)NC(C)C)c2c1CCC2]

a selective beta-2 ($\beta_2$) adrenergic receptor antagonist that binds to the $\beta_2$ receptor subtype with at least 100 times greater affinity than the beta-1 ($\beta_1$) or beta-3 ($\beta_3$) subtypes of the beta adrenoceptor.

Figure 2A:
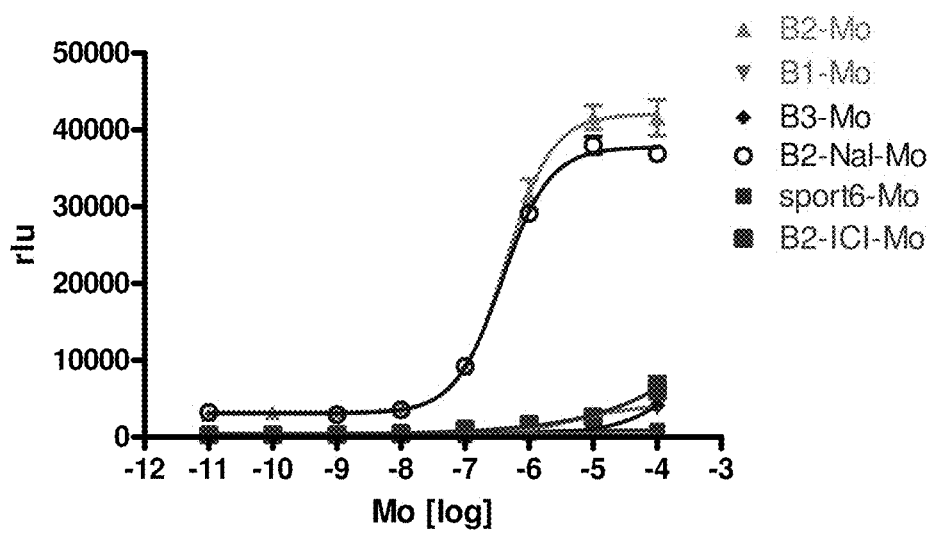
FIG. 2 is a graph of cAMP production as a function of log [morphine], and shows that stimulation of ADRB2 produced much greater morphine dependent increases in cAMP than stimulation of ADRB1 or ADRB3 (FIG. 2A). Although morphine produces dose-dependent increases in intracellular cAMP accumulation by the stimulation of all three ADRBs, morphine is approximately 500-1000 times more potent and shows about 10 times higher intrinsic activity at ADRB2 as compared to agonist properties at ADRB1 and ADRB3 (cf.
Figure 2B:
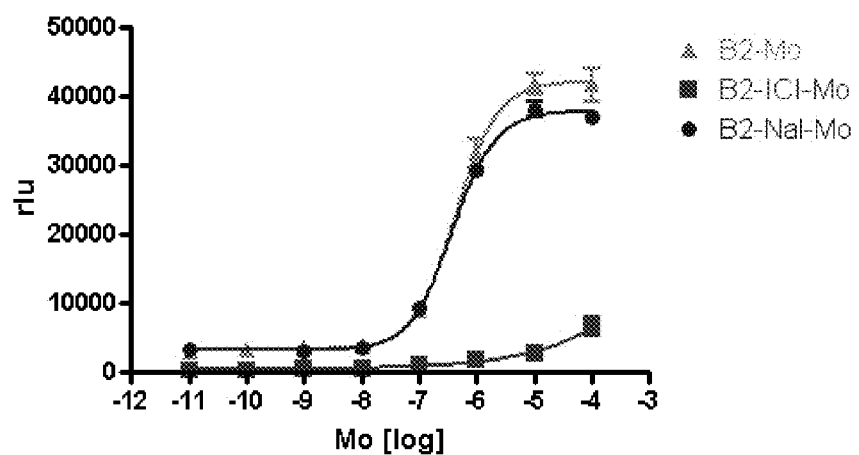
Figure 2C:
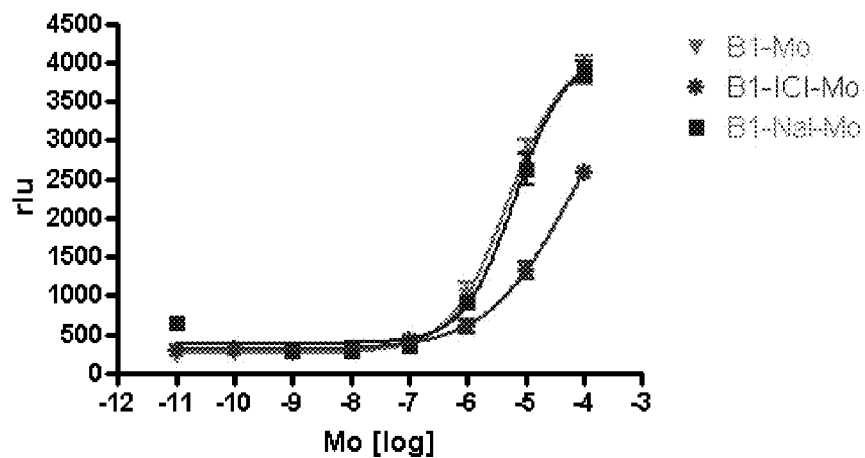
Figure 2D:
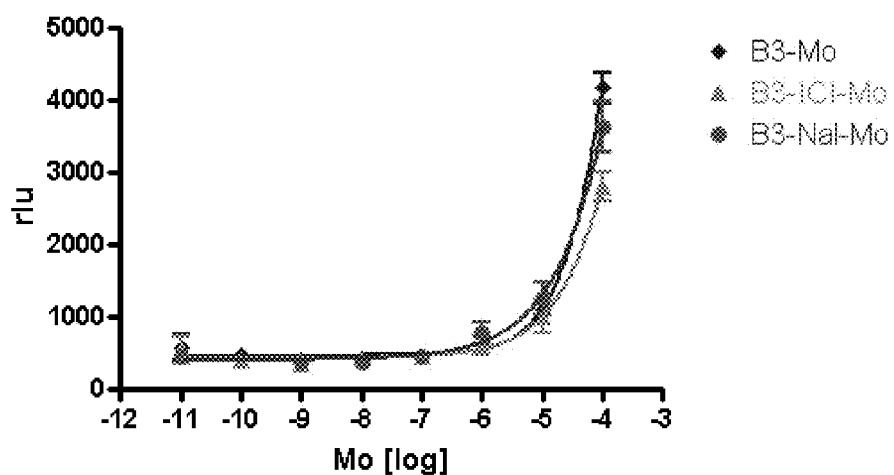

FIG. 2 is a graph of cAMP production as a function of log [morphine], and shows that stimulation of ADRB2 produced much greater morphine dependent increases in cAMP than stimulation of ADRB1 or ADRB3 (FIG. 2A). Although morphine produces dose-dependent increases in intracellular cAMP accumulation by the stimulation of all three ADRBs, morphine is approximately 500-1000 times more potent and shows about 10 times higher intrinsic activity at ADRB2 as compared to agonist properties at ADRB1 and ADRB3 (cf. FIGS. 1B, 1C, and 1D). The stimulation by morphine was completely blocked by the selective ADRB2 antagonist ICI118,551 (300 nM) in cells transfected with ADRB2, produces a partial blockade in cells transfected with ADRB1-dependent stimulation, and no blockade in cells transfected with ADRB3. These effects were ADRB-mediated because morphine did not evoke responses in cells transfected with only Sport6 vector without inserts.

Figure 3:
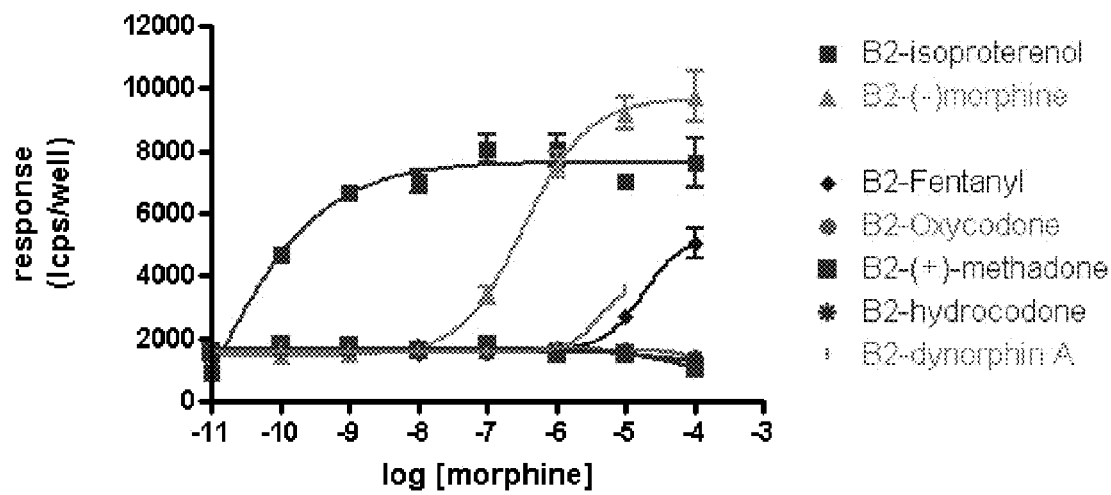
FIG. 3 is a graph of response (lcps/well) as a function of log [morphine] for various opioid agents, including isoproterenol, morphine, fentanyl, oxycodone, methadone, hydrocodone, and dynorphin A, showing that morphine is the most potent ADRB2 agonist in comparison with other opioid agonists.

FIG. 3 is a graph of response (lcps/well) as a function of log [morphine] for various opioid agents, including isoproterenol, morphine, fentanyl, oxycodone, methadone, hydrocodone, and dynorphin A, showing that morphine is the most potent ADRB2 agonist in comparison with other opioid agonists. Although isoproterenol is a more potent agonist of ADRB2 compared to morphine, morphine is a much more potent ADRB2 agonist than other examined opioids. Among 9 tested opioid peptides ($\alpha$- and $\beta$-neo-endorphins, [Leu$^5$] and [Met$^5$] enkephalins, $\beta$-endorphin, dynorphin A and B, Endomorphin-1 and 2; not shown) and four of the most clinically used small molecule opioid agonists, only dynorphin A and fentanyl showed agonistic properties towards ADRB2. These effects were dependent on ADRB2 tranfection (data not shown).

Figure 4:
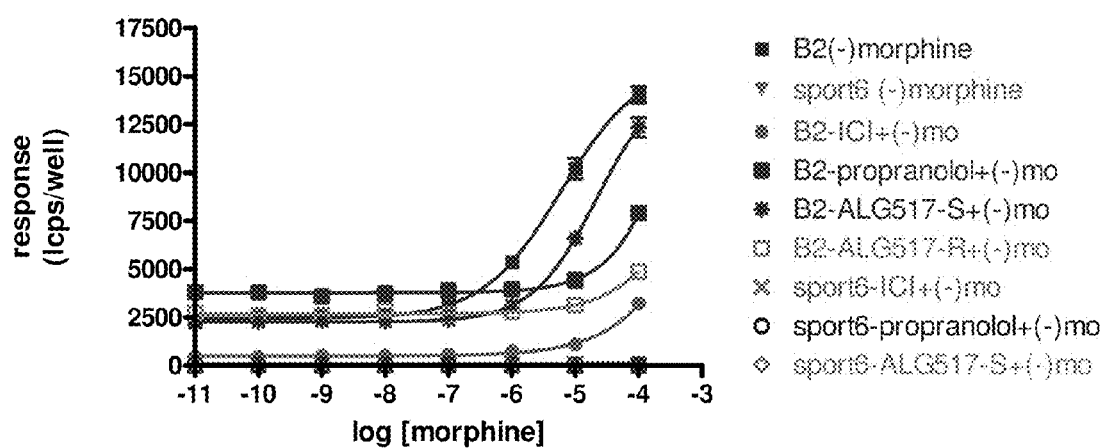
FIG. 4 is a graph of response (lcps/well) as a function of log [morphine] for R-tert-butyl[3-(2-chloro-5-methylphenoxy)-2-hydroxypropyl]amine, denoted as ALG517. The results show that the R isomer of ALG517 is a strong antagonist of stimulated ADRB2-dependent cAMP generation.

FIG. 4 is a graph of response (lcps/well) as a function of log [morphine] for R-tert-butyl[3-(2-chloro-5-methylphenoxy)-2-hydroxypropyl]amine, denoted as ALG517. The results show that the R isomer of ALG517 is a strong antagonist of stimulated ADRB2-dependent cAMP generation. Both the R isomer and S isomer of ALG517 (100 nM) blocked evoked ADRB2-dependent cAMP accumulations, but the R isomer was approximately 30 times more potent an antagonist as compared with the S isomer, and almost 10 times more potent an antagonist as compared with the clinically used non-selective ADRB2 antagonist propranolol (100 nM), and slightly less potent than the selective ADRB2 antagonist ICI118,551 (300 nM). These effects were dependent on transfection of ADRB2 (Sport6-mo—cellular effects in cells transfected with the Sport6 vector having no inserts and stimulated with morphine).

Example 2

Experimental Procedure

Mice were placed atop a glass floor within 20-cm high Plexiglas cylinders (15 cm diameter) and habituated for at least 30 minutes. Mice were briefly removed, and 25 µl of a 2.5% formaldehyde solution was injected subcutaneously into the plantar surface of the right hind paw using a 50 µl microsyringe with a 30-gauge needle. After being returned to the cylinder, each mouse was videotaped from below for the next 60 minutes, and the presence or absence of licking/biting of the right hind paw was sampled once per minute by a blinded observer using The Observer (Noldus Inc.). The early/acute phase of the biphasic formalin test was defined conservatively as the first 5 min of observation, and the late/tonic phase as the last 50 minutes of observation. The R and S isomers of tert-butyl[3-(2-chloro-5-methylphenoxy)-2-hydroxypropyl]amine were evaluated at dosages of 3 mg/kg and 10 mg/kg, against propranolol at 10 mg/kg, and a saline control.

Figure 5:
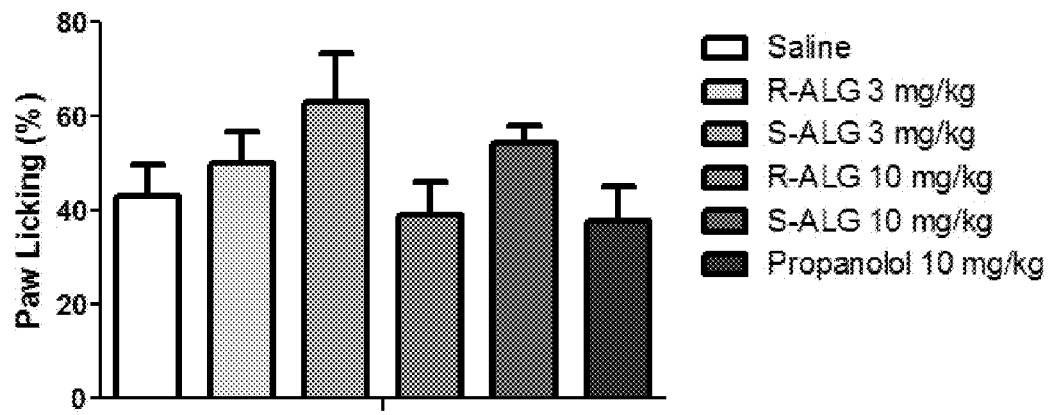
FIG. 5 is a bar graph showing data from a hind paw formalin test (early phase data in FIG. 5a and late phase data in FIG. 5b), presented as a paw licking percentage, for R and S isomers of tert-butyl[3-(2-chloro-5-methylphenoxy)-2-hydroxypropyl]amine at dosages of 3 mg/kg and 10 mg/kg, against propranolol at 10 mg/kg, and a saline control.
Figure 5:
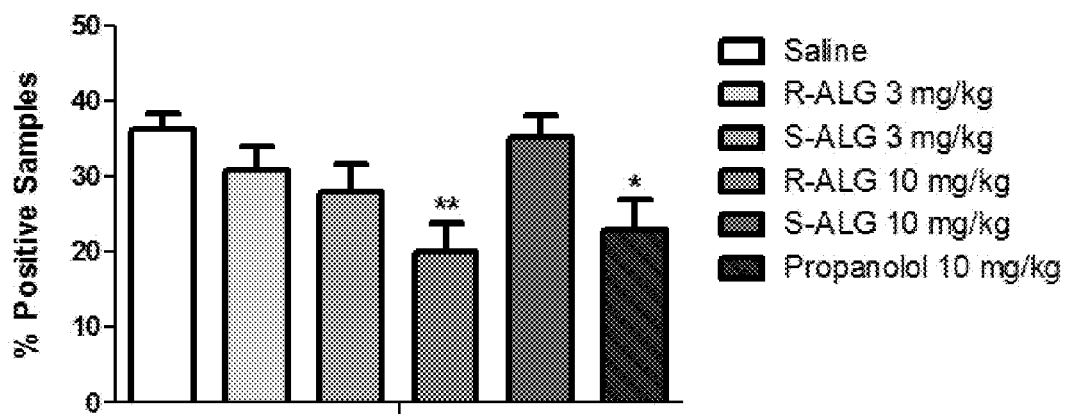

The results are shown in FIG. 5, wherein R-tert-butyl[3-(2-chloro-5-methylphenoxy)-2-hydroxypropyl]amine is denoted as R-ALG, and S-tert-butyl[3-(2-chloro-5-methylphenoxy)-2-hydroxypropyl]amine is denoted as S-ALG. FIG. 5A shows the early phase results of the test, and FIG. 5B shows the late phase results of the test. The data show that the R stereoisomer of tert-butyl[3-(2-chloro-5-methylphenoxy)-2-hydroxypropyl]amine (10 mg/kg) and the non-selective ADRB antagonist propranolol (10 mg/kg) reduced the late phase, C-fiber mediated responses to the hind paw formalin test. Responses recorded during the early, A-delta mediated phase of the procedure were not altered by either test compound. The S stereoisomer of tert-butyl[3-(2-chloro-5-methylphenoxy)-2-hydroxypropyl]amine was without effect at the doses examined (3 and 10 mg/kg).

Example 3

Interrelationship of 6TM MOR and $\beta_2$-Adrenergic Receptor

Figure 6:
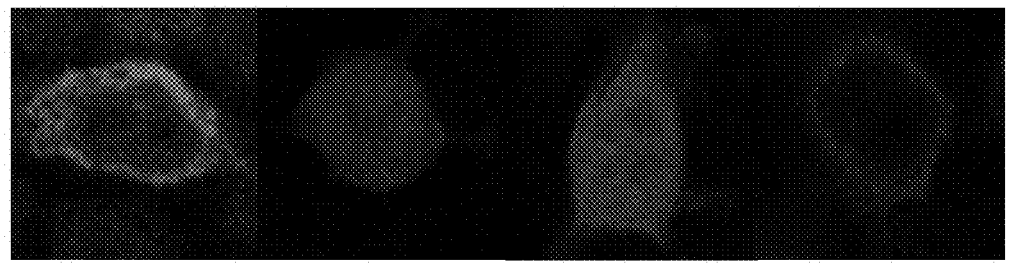
FIG. 6 shows photomicrographs of HEK293 cells in which: the cells were transfected with mu-opioid receptor 7TM and stained for 7TM (FIG. 6(A)); the cells were transfected with mu-opioid receptor 6TM and stained for 6TM (FIG. 6(B)); the cells were transfected with mu-opioid receptor 6TM and 7TM, and stained for 6TM (FIG. 6(C)); and the cells were transfected with mu-opioid receptor 6TM and ADRB2, and stained for 6TM (FIG. 6(D)).

Empirical work was carried out to demonstrate that the $\beta_2$-adrenergic receptor (ADRB2) facilitates cell surface expression of 6-transmembrane (6TM) mu-opioid receptor (MOR), and that ADRB2 physically interacts with 6TM MOR, whereby cellular activities of ADRB2 and 6TM MOR are interdependent in character. FIG. 6 shows confocal images of C-terminally MYC-tagged MOR1 (7TM) or FLAG-tagged MOR1K (6TM) overexpressed in HEK293 cells and stained with either Anti-MYC-Tag Antibody (Alexa Fluor 647 Conjugate) or Anti-DYKDDDDK Tag Antibody (Alexa Fluor 555 conjugate).

More specifically, FIG. 6 shows photomicrographs of HEK293 cells in which: the cells were transfected with mu-opioid receptor 7TM and stained for 7TM (FIG. 6(A)); the cells were transfected with mu-opioid receptor 6TM and stained for 6TM (FIG. 6(B)); the cells were transfected with mu-opioid receptor 6TM and 7TM, and stained for 6TM (FIG. 6(C)); and the cells were transfected with mu-opioid receptor 6TM and ADRB2, and stained for 6TM (FIG. 6(D)).

Cells transfected with MOR1 (FIG. 6A) showed membrane expression of receptor, while cell transfected with MOR1K along (FIG. 6B) or with MOR1 (FIG. 6C) expressed receptor only intracellularly. However, co-expression of the receptor with $\beta_2$AR showed membrane expression of the MOR1K receptor.

These data demonstrate the successful heterologous surface expression of a MOR1K receptor isoform and reveal that persistent physical association with $\beta_2$AR can control MOR1K surface expression. The data evidence the feasibility of controlling activity of the MOR1K receptor isoform by controlling expression and/or activity of $\beta_2$AR.

Example 4

Rotarod Test

The drug effect on motor coordination was tested in the rotarod test using an accelerating rotarod treadmill (Acceler Rota-Rod 7650, Ugo Basile, Varese, Italy) for mice (diameter 3.5 cm) (Jones and Roberts, 1968). The mice were placed on the rotarod, which accelerated from 4 to 40 rpm over a period of 5 min, and the time spent on the rotating drum was recorded for each mouse. On the test day, one preinjection trial (drug-free) was performed before the animals were treated with either saline, R-ALG 517, S-ALG 517 or propanolol (60 mg/kg; 10 ml/kg; n=4/group). Performance was indicated by the latency to fall from the rotarod at 20, 40, 60 and 80 min after injection. R-tert-butyl[3-(2-chloro-5-methylphenoxy)-2-hydroxypropyl]amine is denoted as R-ALG 517, and S-tert-butyl[3-(2-chloro-5-methylphenoxy)-2-hydroxypropyl]amine is denoted as S-ALG 517.

Figure 7:
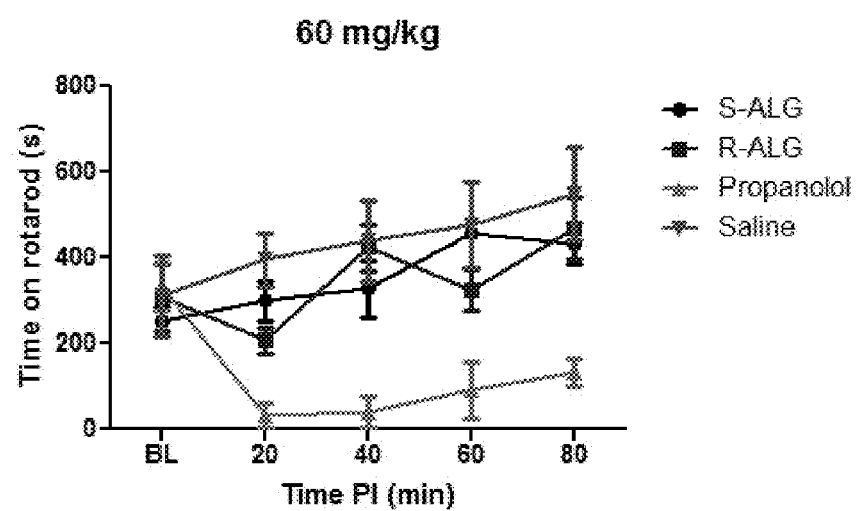
FIG. 7 is a graph of time on rotarod, in seconds, as a function of time, in minutes, for mice administered 60 mg/kg doses of S-ALG 517, R-ALG 517 and propranolol, respectively. The results show that S-ALG 517 and R-ALG 517 produced only slight and possibly not even significant ataxia on the rotarod test, while the mice dosed with 60 mg/kg of propranolol were observed to fall off the rotarod very rapidly.

The results of this test are shown in FIG. 7, and demonstrate that 60 mg/kg doses of S- and R-ALG 517 produced only slight and possibly not even significant ataxia on the rotarod test, while the animal subjects dosed with 60 mg/kg of propranolol were observed to fall off the rotarod very rapidly.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of combating a somatosensory disorder in a subject, comprising administering to the subject an effective amount of a composition comprising bupranolol, wherein the bupranolol is homoenantiomeric in the R isomer, and/or a pharmaceutically acceptable derivative thereof.

2. The method of claim 1, wherein the somatosensory disorder is selected from the group consisting of chronic pain conditions, idiopathic pain conditions, fibromyalgia syndrome, myofascial pain disorders, tension headache, migraine headache, phantom limb sensations, irritable bowel syndrome, chronic lower back pain, back pain, chronic fatigue syndrome, multiple chemical sensitivities, temporomandibular joint disorder, post-traumatic stress disorder, chronic idiopathic pelvic pain, Gulf War Syndrome, vulvar vestibulitis, osteoarthritis, rheumatoid arthritis, neuropathic pain, and angina pectoris.

3. The method of claim 1, wherein the composition comprises a pharmaceutically acceptable derivative of bupranolol.

4. The method of claim 3, wherein the pharmaceutically acceptable derivative of bupranolol is selected from the group consisting of pharmaceutically acceptable bupranolol salts, bupranolol esters, bupranolol solvates, and prodrugs of bupranolol.

5. The method of claim 3, wherein the pharmaceutically acceptable derivative of bupranolol is selected from the group consisting of pharmaceutically acceptable bupranolol salts and bupranolol esters.

6. The method of claim 1, wherein said administering comprises oral administration.

7. The method of claim 1, wherein said administering comprises parenteral administration.

8. The method of claim 1, wherein said administering comprises non-parenteral administration.

9. The method of claim 1, wherein said administering comprises transdermal administration.

10. The method of claim 1, wherein said administering comprises injection administration.

11. The method of claim 1, wherein the composition further comprises an opioid receptor agonist or antagonist.

12. The method of claim 1, wherein the composition further comprises morphine.

13. The method of claim 1, wherein the administering further comprises contemporaneously administering an opioid receptor agonist or antagonist.

14. The method of claim 1, wherein the subject is identified by a screening process comprising referential genotypic screening indicative of susceptibility to the somatosensory disorder.

15. The method of claim 14, wherein said referential genotypic screening indicative of susceptibility to a somatosensory disorder comprises:
   determining a genotype of a candidate subject with respect to a gene selected from the group consisting of ADRB2, ADRB3, COMT, and combinations thereof; and
   comparing the genotype of the candidate subject with at least one reference genotype associated with the susceptibility to develop the somatosensory disorder,
   wherein the reference genotype is selected from the corresponding group consisting of an ADRB2 genotype, an ADRB3 genotype, a COMT genotype, and combinations thereof.

16. The method of claim 15, wherein the somatosensory disorder is selected from the group consisting of chronic pain conditions, idiopathic pain conditions, fibromyalgia syndrome, myofascial pain disorders, tension headache, migraine headache, phantom limb sensations, irritable bowel syndrome, chronic lower back pain, back pain, chronic fatigue syndrome, multiple chemical sensitivities, temporomandibular joint disorder, post-traumatic stress disorder, chronic idiopathic pelvic pain, Gulf War Syndrome, vulvar vestibulitis, osteoarthritis, rheumatoid arthritis, neuropathic pain, and angina pectoris.

17. A method of combating hyperalgesia incident to administration of an opioid receptor agonist to a subject, comprising contemporaneously administering to said subject an effective amount to combat said hyperalgesia, of homoenantiomeric R-tert-butyl[3-(2-chloro-5-methylphenoxy)-2-hydroxypropyl]amine, or a derivative thereof.

18. The method of claim 17, wherein said administering comprises administration of a salt, ester or solvate of R-tert-butyl[3-(2-chloro-5-methylphenoxy)-2-hydroxypropyl]amine.

19. A method of modulating ADRB2 and 6TM MOR interaction to mediate analgesia in a subject, comprising administering to the subject an effective amount therefor of homoenantiomeric R-tert-butyl[3-(2-chloro-5-methylphenoxy)-2-hydroxypropyl]amine, or a derivative thereof.

20. The method of claim 19, wherein said administering comprises administration of a salt, ester or solvate of R-tert-butyl[3-(2-chloro-5-methylphenoxy)-2-hydroxypropyl]amine.

21. The method of claim 1, wherein the composition further comprises a second therapeutic agent selected from the group consisting of: analgesic agents; anti-inflammatory agents; adjunctive analgesics; adrenergic receptor beta-2 antagonists; adrenergic receptor beta-3 antagonists; and catechol-O-methyltransferase modulators.

* * * * *